United States Patent [19]

Hill et al.

[11] Patent Number: 4,902,675
[45] Date of Patent: Feb. 20, 1990

[54] "2-PYRIDYL AND 4-PYRIDYL PHOSPHINE GOLD (I) ANTI TUMOR COMPLEXES"

[75] Inventors: David T. Hill, North Wales; Randall K. Johnson, Ardmore, both of Pa.

[73] Assignee: SmithKline Beckman Corporation, Philadelphia, Pa.

[21] Appl. No.: 848,670

[22] Filed: Apr. 4, 1986

Related U.S. Application Data

[63] Continuation-in-part of Ser. No. 829,359, Feb. 14, 1986, abandoned, which is a continuation-in-part of Ser. No. 734,524, May 16, 1985, abandoned.

[51] Int. Cl.$^4$ .................... C07F 1/12; A61K 31/555; A61K 31/70
[52] U.S. Cl. .................................. 514/24; 536/17.1; 514/89; 546/2
[58] Field of Search .................. 514/89, 24; 546/2; 536/17.1

[56] References Cited

U.S. PATENT DOCUMENTS 3,661,959 5/1972 Vaughan ........................ 260/430

FOREIGN PATENT DOCUMENTS 0151046 8/1985 European Pat. Off. .
0164970 12/1985 European Pat. Off. .

OTHER PUBLICATIONS

Padzur, Proc. Am. Soc. Clin. Oncol. 3, p. 219 (1984), Abstract C-856.
Schabel, Jr., I, "Cancer-Chemoherapy-Fundimental Concepts . . . ", W3 C162H 1974c (1975), pp. 323,350.
Schahel, Jr. II, Pharma. ther. A, 1, 411, 412, 417 (1977).
Martin, Cancer Research 46, 2189 (1986).
Cariati et al, Inorg. Chim. Acta, 1(2), 315–318 (1967).
McAuliffe, J. C. S., Dalton, 1730–1735 (1979).
Bates et al., Inorg. Chim. Acta, 81(2), 151–156 (1984).
Weinstock et al., J. Med. Chem., 7(1), 139–140 (1971).
Van de Vondel et al., Physica Scripta., 16(5–6), 364–366.
Struck et al., J. Med. Chem., 9, 414–416 (1966).
Mirabelli et al., Proceedings of AACR Mar. 1984, No. 1455, p. 367 (1984).
Mirabelli et al., Cancer Research, 45, 32–39 (1985).
Johnson et al., Proceedings of AACR Mar. 1985, No. 1001, p. 254 (1985).
Snyder et al., Proceedings of AACR Mar. 1985, No. 1007, p. 255 (1985).
Mirabelli et al., Proceedings of AACR Mar. 1985, No. 1008, p. 256 (1985).
Shaw et al., Inorganica Chimica Acta, 123, 213–216 (1986).
Eggleston et al., Inorganica Chimica Acta, 108, 221–226 (1985).
Mirabelli et al., Biochemical Pharmacology, 35(9), 1435–1443 (1986).
Mirabelli et al., Biochemical Pharmacology, 35(9), 1427–1433 (1986).
Mirabelli et al., J. Med. Chem., 39(2), 218–223 (1986).
Hill et al., Abstract #204, American Chemical Society.
Berners-Price et al., Abstract #244 American Chemical Society.
Mirabelli et al., Abstract #1114, Proceedings of AACR 27, Mar. 1986.
Johnson et al., Abstract #1115, Proceedings of AACR, 27 Mar. 1986.
Hill et al., Abstract #14, 190th American Chemical Society National Meeting.

Primary Examiner—Mark L. Berch
Attorney, Agent, or Firm—Carol G. Canter; Edward T. Lentz; Alan D. Lourie

[57] ABSTRACT

2-pyridyl and 4-pyridyl phosphine gold compounds of the formula:

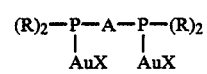

and 2-pyridyl phosphine gold compounds of the formula:

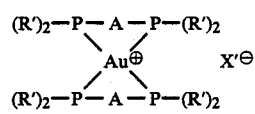

and pharmaceutical compositions containing an effective, tumor cell growth-inhibiting amount of such a compound.

20 Claims, No Drawings

"2-PYRIDYL AND 4-PYRIDYL PHOSPHINE GOLD (I) ANTI TUMOR COMPLEXES"

CROSS-REFERENCE TO RELATED APPLICATION

This is a continuation-in-part of application Ser. No. 829,359, filed Feb. 14, 1986, which is abandoned, which is a continuation-in-part of application Ser. No. 734,524, filed May 16, 1985, which is abandoned.

BACKGROUND OF THE INVENTION

This invention relates to novel 2-pyridyl and 4-pyridyl phosphine gold(I) compounds which have tumor cell growth-inhibiting activity, pharmaceutical compositions containing an effective tumor cell growth-inhibiting amount of such a novel compound, and a method for treating tumor cells sensitive to such a compound by administering tumor cell growth-inhibiting amounts of such a novel compound to a host animal affected by such tumor cells.

The 2-pyridyl and 4-pyridyl gold complexes of this invention are not known. Cariati et al., *Inorg. Chim. Acta*, 1(2), 315–18 (1967), Bates et al., *Inorg. Chim. Acta*, 81 (2), 151–156 (1984) and McAuliffe et al., *J. C. S. Dalton*, 1730 (1979), disclose bis[1,2-bis(diphenylphosphino)ethane]gold(I) chloride. Struck et al., *J. Med. Chem.*, 9, 414–416 (1966), disclose cytotoxic activity for 1,2-bis(diphenylphosphino)ethane. None of the aforementioned references disclose or suggest the compounds, pharmaceutical compositions or methods of treatment of the instant invention.

SUMMARY OF THE INVENTION

This invention relates to 2-pyridyl and 4-pyridyl gold (I) compounds of the formula

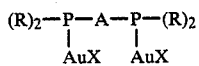

FORMULA (I)

wherein:

R is the same and is 2-pyridyl or 4-pyridyl;

A is a straight or branched alkanediyl chain of from one to six carbon atoms; and X is the same and is halo or thiosugar. When X is thiosugar, the attachment of X to the gold atom is through the sulfur atom of the thiosugar.

This invention also relates to 2-pyridyl phosphine gold compounds of the formula:

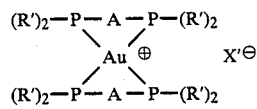

FORMULA (II)

wherein:

R' is the same and is 2-pyridyl;

A is the same and is a straight or branched alkanediyl chain of from one to six carbon atoms; and X' is the same and is halo.

This invention also relates to a pharmaceutical composition which comprises an effective, tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of Formula (I) or Formula (II).

Another aspect of this invention relates to a method of inhibiting the growth of animal tumor cells sensitive to a compound of Formula (I) or Formula (II) which comprises administering to an animal afflicted with said tumor cells, an effective, tumor cell growth-inhibiting amount of a compound of Formula (I) or Formula (II).

DETAILED DESCRIPTION OF THE INVENTION

By the term "thiosugar" is meant any 1-thioaldose. Examples of such thiosugars include 1-thioglucose, 1-thiogalactose, 1-thiomannose, 1-thioribose, 1-thiomaltose, 1-thiofucose, tetra-O-acetyl-1-thioglucose, tetra-O-acetyl-1-thiomannose, tetra-O-acetyl-1-thiogalactose, tri-O-acetyl-1-thioribose, hepta-O-acetyl-1-thiomaltose, and tri-O-acetyl-1-thiofucose.

All the compounds of Formula (I) and Formula (II) can be prepared by methods available to one skilled in the art.

Generally, the starting materials for the Formula (I) compounds wherein X is chloro are the corresponding diphosphino hydrocarbons represented by the following structural formula:

   Formula (IA)

wherein A and R are as defined above. To obtain the digold products of Formula (I), an appropriate diphosphino hydrocarbon intermidiate of Formula (IA) is reacted either directly with chloroauric acid tetrahydrate or a reduced form of the acid hydrate obtained by treatment with thiodiglycol in an appropriate non-reactive organic solvent.

The necessary diphosphino hydrocarbon intermediates of Formula (IA) are prepared by reacting the appropriate bromopyridine compound with n-butyl lithium and the appropriate 1,2-bis(dichlorophosphine)hydrocarbon compound, all of which are available commercially, for example from Strem Chemicals Inc., Newburyport, Mass.

To obtain the Formula (I) compounds wherein X is thiosugar, the appropriate Formula (I) compound wherein X is chloro is reacted with the appropriate sodium thiosugar. The necessary sodium thiosugars are commercially available, for example, from Sigma Chemical Co., St. Louis, Mo.

Formula (I) compounds wherein X is bromo are prepared by reacting the appropriate ligand of Formula (IA) with bromoauric acid hydrate, which is commercially available, for example from Strem Chemicals, Inc., Newburyport, Mass., which has been reduced by treatment with thiodiglycol; or by reacting the appropriate ligand of Formula (IA) with bromoauric acid hydrate directly in an appropriate non-reactive organic solvent. Alternatively, Formula (I) compounds wherein X is bromo are prepared by reacting the appropriate compound of Formula (I), wherein X is chloro, with sodium bromide in an appropriate organic solvent, such as aqueous ethanol or DMF.

Formula (I) compounds wherein X is iodo are prepared by treating the appropriate compound of Formula (I), wherein X is chloro or bromo, with sodium iodide in an appropriate organic solvent such as acetone.

Generally, the Formula (II) compounds can be obtained by reacting the appropriate Formula (I) compound with the appropriate Formula (IA) compound in an appropriate non-reactive organic solvent.

As stated above, the compounds of Formula (I) and Formula (II) have tumor cell growth-inhibiting activity which has been demonstrated in at least one animal tumor model.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of Formula (I) and Formula (II) is demonstrated in the P388 leukemia mouse model employing the following protocol:

$10^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of either N,N-dimethylacetamide (DMA) or 95% ethanol (depending upon solubility). An equal volume of saline is added; if the drug comes out of solution an equal volume of polyethoxylated castor oil is added and then saline qs to a concentration such that the desired dose is delivered in 0.5 ml. The final concentration of DMA, ethanol and polyethoxylated castor oil is ≧10 percent. Dilutions for lower doses are made with saline so there is a decreasing proportion of organic solvents in the vehicle with decreasing dosage. These vehicles provide soluble formulations (or suspensions). Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change (Δ wt.) is used as a reflection of toxicity. Each experiment also includes an inoculum titration-groups of 8 mice inoculated ip with $10^5$ to $10^0$ P388 leukemia cells. The titration is used to calculate cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 9 to 11 days. A drug is considered active if it produces ≧25 percent ILS.

A summary of the evaluation of several compounds of Formula (I) and Formula (II) in the in vivo P388 model is shown in the following Table A.

TABLE A $$(R)_2-P-A-P-(R)_2$$
$$\quad\quad |\quad\quad\quad |$$
$$\quad\quad Aux\quad\quad AuX$$

FORMULA (I)

$$(R')_2-P-A-P-(R')_2$$
$$\quad\quad\quad\quad\backslash\quad\quad /$$
$$\quad\quad\quad\quad\quad Au^{\oplus}\quad\quad X'^{\ominus}$$
$$\quad\quad\quad\quad /\quad\quad\backslash$$
$$(R')_2-P-A-P-(R')_2$$

FORMULA (II)

| Compound Number | Formula Number | R | A | X | MTD[a] (mg/kg) | ILS (max)[b] (%) |
|---|---|---|---|---|---|---|
| 1 | I | 2-pyridyl | (CH$_2$)$_2$ | Cl | 6 | 55/60 |
| 2 | I | 4-pyridyl | (CH$_2$)$_2$ | Cl | 12 | 65/32/28 |
| 3 | II | 2-pyridyl | (CH$_2$)$_2$ | Cl | 8 | 80/75/83/84 |
| 4 | I | 2-pyridyl | (CH$_2$)$_2$ | 1-thio-glucose | 8 | 85/53/56 |

[a] maximally tolerated dose for B62DF female mice on an ip qDX5 regimen.
[b] maximum increase in lifespan produced in mice bearing ip P388 leukemia (figures separated by slashes indicate data generated in separate experiments).

Based on the data set forth in Table A, compounds of Formula (I) and Formula (II) showed significant antitumor activity in the in vivo ip p388 leukemia tumor assay. It should be noted that the 4-pyridyl analog of Compound No. 3 of Table A was also tested twice in the ip P388 leukemia assay, but exhibited insignificant antitumor activity (i.e. <25%) in both tests.

The cytotoxic activity of Compound No. 3 of Table A was evaluated in vivo using B16 melanoma cells. In this system, groups of eight B6D2F$_1$ mice are inoculated ip with 0.5 ml of a 10% (w:v) brei of B16 melanoma prepared from pooled sc tumors excised at 14–21 days from C67B$_1$/6 donor mice. Daily treatment is begun 24 hours after tumor impantation and is continued daily for ten (10) days. The route of drug administration is ip. The mice are monitored daily for survival for sixty (60) days. Antitumor activity is assessed by prolongation of median survival time. An ILS of ≧25% indicates activity in this tumor model.

A summary of the results of the in vivo ip B16 melanoma assay is shown in Table B.

TABLE B

| Compound No.[a] | MTD (mg/kg)[b] | ILS (%)[c] |
|---|---|---|
| 3 | 10 | 43 |

[a] see Table A for structure.
[b] maximally tolerated dose for B6D2F$_1$ mice on an ipqD × 9 regimen (Regimen is preferably qD × 10 but supply of Compound No. 3 was extinguished on day 9).
[c] maximum increase in lifespan produced in mice bearing ip B16 melanoma.

The pharmaceutical compositions of this invention comprise an effective tumor cell growth-inhibiting amount of a compound of Formula (I) or Formula (II) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hyroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., *Cancer Chemo. Rept.,* 50, 219–244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m$^2$ of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, perferably mice.

It will be appreciated that the actual preferred dosages of the compounds of Formula (I) or Formula (II) used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of Formula (I) or Formula (II) contacts the tumor. Optimal dosages for a given set of conditions can be ascertained by those skilled in the art using conventional dosage determination tests in view of the above experimental data. For parenteral administration of a compound of Formula (I) the dose preferably employed is from about 5 to about 20 mg/m$^2$ of body surface per day for five days, repeated about every fourth week for four courses of treatment. For parenteral administration of a compound of Formula (II) the dose generally employed is from about 5 to about 100 mg/m$^2$ of body surface per day for five days, repeated about every fourth week for four courses of treatment.

The method for inhibiting the growth of animal tumor cells sensitive to a compound of Formula (I) or Formula (II) in accordance with this invention comprises administering to a host animal afflicted with said tumor cells, an effective tumor cell growth-inhibiting amount of a compound of Formula (I) or Formula (II).

EXAMPLES

The following examples illustrate the chemical preparation of several compounds of Formula (I) or Formula (II) which are used in the compositions and methods of this invention and as such are not to be construed as limiting the scope thereof. All temperatures are in degrees Centigrade.

EXAMPLE 1

μ-[1,2-Bis(di-2-pyridylphosphino)ethane]bis(-chlorogold)

Under an argon atmosphere, 2-bromopyridine (30.95 g, 0.19 mole) in anhydrous ethyl ether (50 ml) was added to n-butyl lithium (0.19 mole) in hexane (73 ml) keeping the temperature below −50°. After stirring for 1 hour, an additional 7.5 g of 2-bromopyridine was added, and the mixture was stirred for 30 minutes. An ether solution (100 ml) of 1,2-bis(dichlorophosphino)ethane (10 g, 43 mmole), obtained from Strem Chemicals Inc, Newburyport, Mass., was added, and the mixture was stirred for 1 hour at −50°, and then allowed to warm to room temperature overnight. Saturated aqueous ammonium chloride was added, and the mixture was stirred for 1 hour. The solid was collected and dissolved in chloroform, dried (Na$_2$SO$_4$), filtered and the solvent was removed to give a dark residue. The residue was treated with acetone, and the acetone was cooled to give a light yellow solid (4.5 g). Recrystallization from acetone gave 2.64 g of 1,2-bis(di-2-pyridylphosphino)acetone ethane, melting point (m.p.) 134°–135°.

Thiodiglycol (1 g, 8.18 mmole) in water (10 ml)/methanol (30 ml) was added to chloroauric acid tetrahydrate (0.88 g. 2.14 mmole) in water (10 ml) kept at 0°. After stirring for 15 minutes, 1,2-bis(di-2-pyridylphosphino)ethane, phosphino)ethane, (0.43 g, 1.07 mmole), prepared as described above, in acetone (50 ml)/chloroform (10 ml) was added, and the mixture was stirred for 2 hours. Methanol was added, and the product was collected and slurried with CH$_2$Cl$_2$/CHCl$_3$, diluted with methanol and cooled. The resulting solid was collected and dried to give 0.38 g (41%) of the named product, m.p. 292°–293°.

EXAMPLE 2

μ-[1,2-Bis(di-2-pyridylphosphino)ethane]bis[(1-thio-β-D-glucopyranosato-S)gold

A mixture of sodium thioglucose (0.33 g, 1.5 mmole) obtained from Sigma Chemical Company, St. Louis, Mo., and μ-[1,2-bis(di-2-pyridylphosphino)-ethane]bis(-chlorogold) (0.6 g, 0.69 mole), prepared as described in Example 1, in chloroform (75 ml)/methanol (75 ml)/water (10 ml) was stirred at ambient temperature for 2 hours and the solvent evaporated. The residue was dissolved in chloroform and the precipitate was collected. The solid was dissolved in methanol, filtered and the solvent evaporated. The residue was dissolved in acetone, cooled, and the precipitate was collected and dried to give 0.49 g (60%) of the named compound as a white, amorphous solid.

EXAMPLE 3

μ-[1,2-Bis(di-4-pyridylphosphino)ethane]bis(-chlorogold).

Under an argon atmosphere, 4-bromopyridine (30.95 g, 0.19 mole) in anhydrous ethyl ether (50 ml) was added to n-butyl lithium (0.19 mole) in hexane (73 ml) keeping the temperature below −50°. After stirring for 1 hour, an additional 7.5 g of 4- bromopyridine was added, and the mixture was stirred for 30 minutes. An ether solution (100 ml) of 1,2-bis(dichlorophosphino)ethane (10 g, 43 mmole), obtained from Strem Chemicals Inc., Newburyport, Mass., was added and the mixture was stirred for 1 hour at −50°, and then allowed to warm to room temperature overnight. After 18 hours at ambient temperature, aqueous saturated ammonium chloride was added and the solid removed. The residual solid in the flask was collected, dissolved in chloroform, treated with activated carbon, filtered, and then the solvent was removed. Flash chromatography (SiO$_2$, 7% methanol/methylene chloride) of the residue gave a small amount of 1-2-bis(di-4-pyridylphosphino)ethane, m.p. 183°-185°.

Thiodiglycol (2 g, 16.4 mmole) in water (10 ml)/methanol (30 ml) was added to chloroauric acid tetrahydrate (1.58 g, 3.83 mmole) in water (10 ml) kept at 0°. After stirring for 15 minutes, 1,2-bis(di-4-pyridylphosphino)ethane (0.77 g, 1.9 mmole), prepared as described above, in CH$_2$Cl$_2$ (10 ml)/methanol (30 ml) was added and the mixture allowed to stir for 1 hour. Methanol was added, and the precipitate collected and stirred in acetonitrile, filtered and dried to give 0.75 g (45%) of the named product, m.p. 241°-242°.

EXAMPLE 4

Chlorobis[1,2-bis(di-2-pyridylphosphino)ethane]gold

A solution of 1,2-bis(di-2-pyridylphosphino)ethane (0.17 g, 0.42 mmole), prepared as described in Example 1, in CH$_2$Cl$_2$ (25 ml) was added to a suspension of μ-[1,2-bis(di-2-pyridylphosphino)ethane]bis(chlorogold) (0.12 g, 0.14 mmole) in CH$_2$Cl$_2$ (25 ml), and the mixture was stirred at ambient temperature for 18 hours giving a clear solution. The solvent was evaporated, and the residue was dissolved in methanol and diluted with ethyl ether. After cooling, the precipitate was collected and dried to give 0.28 g (98%) of the named product, m.p. 257°-258°.

EXAMPLE 5

(a) Using the procedure outlined in Example 1 or Example 3, by directly reacting the appropriate haloauric acid hydrate with the appropriate diphosphino hydrocarbon compound of Formula (IA) in an appropriate non-reactive organic solvent or by reacting the appropriate haloauric acid hydrate which has been reduced by treatment with thiodiglycol with the appropriate compound of Formula (I), the following Formula (I) compounds wherein X is chloro or bromo are prepared; or by reacting the appropriate Formula (I) compound wherein X is chloro with sodium bromide in an appropriate organic solvent, such as aqueous ethanol or DMF, the following Formula (I) compounds wherein X is bromo are prepared; and by reacting the appropriate Formula (I) compound wherein X is chloro or bromo with sodium iodide in an appropriate organic solvent, such as acetone, the following Formula (I) compounds wherein X is iodo are prepared.

(i)    μ-[1,1-Bis(di-2-pyridylphosphino)methane]bis-(chlorogold)
    (ii)    μ-[1,3-Bis(di-2-pyridylphosphino)propane]bis-(chlorogold)
    (iii)    μ-[1,4-Bis(di-2-pyridylphosphino)butane]bis-(chlorogold)
    (iv)    μ-[1,5-Bis(di-2-pyridylphosphino)pentane]bis-(chlorogold)
    (v)    μ-[1,6-Bis(di-2-pyridylphosphino)hexane]bis-(chlorogold)
    (vi)    μ-[1,2-Bis(di-2-pyridylphosphino)ethane]bis-(bromogold)
    (vii)    μ-[1,2-Bis(di-2-pyridylphosphino)ethane]bis-(iodogold)
    (viii)    μ-[1,2-Bis(di-4-pyridylphosphino)methane]bis-(chlorogold)
    (ix)    μ-[1,2-Bis(di-4-pyridylphosphino)propane]bis-(chlorogold)
    (x)    μ-[1,2-Bis(di-4-pyridylphosphino)butane]bis-(chlorogold)
    (xi)    μ-[1,2-Bis(di-4-pyridylphosphino)pentane]bis-(chlorogold)
    (xii)    μ-[1,2-Bis(di-4-pyridylphosphino)hexane]bis-(chlorogold)
    (xiii)    μ-[1,2-Bis(di-4-pyridylphosphino)ethane]bis-(bromogold)
    (xiv)    μ-[1,2-Bis(di-4-pyridylphosphino)ethane]bis-(iodogold)

(b) Using the procedure outlined in Example 4, by reacting the appropriate Formula (I) compound, wherein R is 2-pyridyl, prepared as described above, with the appropriate Formula (IA) compound, prepared as described above, the following Formula (II) compounds are prepared:

(i)    Chlorobis[1,1-bis(di-2-pyridylphosphino)methane] gold
    (ii)    Chlorobis[1,3-bis(di-2-pyridylphosphino)propane] gold
    (iii)    Chlorobis[1,4-bis(di-2-pyridylphosphino)butane] gold
    (iv)    Chlorobis[1,5-bis(di-2-pyridylphosphino)pentane] gold
    (v)    Chlorobis[1,6-bis(di-2-pyridylphosphino)hexane] gold
    (vi)    Iodobis[1,2-bis(di-2-pyridylphosphino)ethane] gold
    (vi)    Bromobis[1,2-bis(di-2-pyridylphosphino)ethane] gold

EXAMPLE 6

Using the procedure of Example 2, by reacting the appropriate Formula (I) compound wherein X is chloro, prepared according to the procedure of Example 1, 3 or 5, with the appropriate thiosugar, the following Formula (I) compounds wherein X is thiosugar are prepared:

(a)    μ-[1,1-bis(di-2-pyridylphosphino)methane]bis-(1-thio-β-D-glucopyranosato-S)gold
    (b)    μ-[1,3-bis(di-2-pyridylphosphino)propane]bis-(1-thio-62 -D-glucopyranosato-S)gold
    (c)    μ-[1,4-bis(di-2-pyridylphosphino)butane]bis-(1-thio-β-D-glucopyranosato-S)gold
    (d)    μ-[1,5-bis(di-2-pyridylphosphino)pentane]bis-(1-thio-β-D-glucopyranosato-S)gold
    (e)    μ-[1,6-bis(di-2-pyridylphosphino)hexane]bis-(1-thio-β-D-glucopyranosato-S)gold
    (f)    μ-[1,2-bis(di-2-pyridylphosphino)ethane]bis-(1-thio-β-D-galactopyranosato-S)gold
    (g)    μ-[1,2-bis(di-2-pyridylphosphino)ethane]bis-(1-thio-α-D-mannopyranosato-S)gold
    (h)    μ-[1,2-bis(di-2-pyridylphosphino)ethane]bis-(1-thio-D-ribofuranosato-S)gold
    (i)    μ-[1,1-bis(di-4-pyridylphosphino)methane]bis-(1-thio-β-D-glucopyranosato-S)gold
    (j)    μ-[1,2-bis(di-4-pyridylphosphino)ethane]bis-(1-thio-62 -D-glucopyranosato-S)gold
    (k)    μ-[1,3-bis(di-4-pyridylphosphino)propane]bis-(1-thio-β-D-glucopyranosato-S)gold
    (l)    μ-[1,4-bis(di-4-pyridylphosphino)butane]bis-(1-thio-β-D-glucopyranosato-S)gold
    (m)    μ-[1,5-bis(di-4-pyridylphosphino)pentane]bis-(1-thio-β-D-glucopyranosato-S)gold
    (n)    μ-[1,6-bis(di-4-pyridylphosphino)hexane]bis-(1-thio-β-D-glucopyranosato-S)gold
    (o)    μ-[1,2-bis(di-4-pyridylphosphino)ethane]bis-(1-thio-β-D-galactopyranosato-S)gold (p) μ-[1,2-bis(di-4-pyridylphosphino)ethane]bis-(1-thio-α-D-mannopyranosato-S)gold (q) μ-[1,2-bis(di-4-pyridylphosphino)ethane]bis-(1-thio-D-ribofuranosato-S)gold

EXAMPLE 7

As a specific embodiment of a composition of this invention, an active ingredient, such as one part of the compound of Example 1, is dissolved in 5 parts of dimethylacetamide and 5 parts of polyethoxylated castor oil and then normal saline solution qs, and is administered parenterally in one dose of 5 mg/m2 to a host animal afflicted with tumor cells sensitive to that compound.

What is claimed is:

1. A compound of the formula:

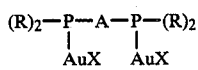

wherein:

R is 2-pyridyl or 4-pyridyl;

A is a straight or branched alkanediyl chain of from one to six carbon atoms; and X is halo or thiosugar.

2. The compound of claim 1 wherein A is ethane-1,2-diyl and R is the same and is 2-pyridyl.

3. The compound of claim 2 wherein X is chloro.

4. The compound of claim 2 wherein X is 1-thioglucose.

5. The compound of claim 1 wherein A is ethane-1,2-diyl and R is the same and is 4-pyridyl.

6. The compound of claim 5 wherein X is chloro.

7. A compound of the formula:

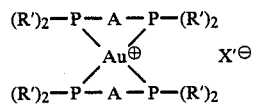

wherein

R' is 2-pyridyl;

A is a straight or branched alkanediyl chain of from one to six carbon atoms; and X' is halo.

8. The compound of claim 7 wherein A is ethane-1,2-diyl and X' is chloro.

9. A pharmaceutical composition which comprises an effective tumor cell-growth inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of claim 1.

10. The composition of claim 9 wherein A is ethane-1,2-diyl and R is the same and is 2-pyridyl.

11. The composition of claim 10 wherein X is chloro.

12. The composition of claim 10 wherein X is 1-thioglucose.

13. The composition of claim 9 wherein A is ethane-1,2-diyl and R is the same and is 4-pyridyl.

14. The composition of claim 13 wherein X is chloro.

15. The composition of claim 9 wherein the composition is in a dosage unit form adapted for parenteral administration.

16. The composition of claim 15 wherein the parenteral dosage unit is adapted to administer from about 5 to about 20 mg/m² of body surface.

17. A pharmaceutical composition which comprises an effective tumor cell-growth inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of claim 7.

18. The composition of claim 17 wherein A is ethane-1,2-diyl and X' is chloro.

19. The composition of claim 17 wherein the composition is in a dosage unit form adapted for parenteral administration.

20. The composition of claim 19 wherein the parenteral dosage units is adapted to administer from about 5 to about 100 mg/m² of body surface.

* * * * *